(12) United States Patent
Hercules

(10) Patent No.: US 7,172,530 B1
(45) Date of Patent: Feb. 6, 2007

(54) METHOD AND APPARATUS FOR MONITORING AND IMPROVING EXERCISE SCHEDULE COMPLIANCE

(76) Inventor: Jesse Thomas Hercules, 308 Wishing Tree La., Oxford, MS (US) 38655

( * ) Notice: Subject to any disclaimer, the term of this patent is extended or adjusted under 35 U.S.C. 154(b) by 0 days.

(21) Appl. No.: 11/164,911

(22) Filed: Dec. 9, 2005

(51) Int. Cl.
*A63B 21/00* (2006.01)
*A61B 5/00* (2006.01)

(52) U.S. Cl. .............................. 482/4; 482/8; 600/300; 434/247

(58) Field of Classification Search ................ 482/1–9, 482/900–902; 600/300, 595; 434/236, 247; 705/2
See application file for complete search history.

(56) References Cited

U.S. PATENT DOCUMENTS

| | | | |
|---|---|---|---|
| 5,673,691 A | 10/1997 | Abrams et al. | |
| 5,890,997 A | 4/1999 | Roth | |
| 5,954,510 A * | 9/1999 | Merrill et al. | .............. 434/236 |
| 6,039,688 A | 3/2000 | Douglas et al. | |
| 6,077,193 A | 6/2000 | Buhler et al. | |
| 6,283,914 B1 | 9/2001 | Mansfield et al. | |
| 6,513,532 B2 | 2/2003 | Mault et al. | |
| 6,607,483 B1 * | 8/2003 | Holland | ...................... 600/300 |
| 6,632,158 B1 * | 10/2003 | Nashner | ......................... 482/8 |
| 6,643,385 B1 | 11/2003 | Bravomalo | |
| 2002/0107704 A1 | 8/2002 | Spyker | |
| 2004/0102391 A1 | 5/2004 | Ellis et al. | |
| 2004/0116780 A1 | 6/2004 | Brown | |

\* cited by examiner

*Primary Examiner*—Glenn E. Richman
(74) *Attorney, Agent, or Firm*—Clausen Miller, PC

(57) ABSTRACT

A computer-based system for monitoring and improving a user's exercise compliance by providing the user with multiple forms of feedback designed to encourage adherence to an exercise schedule. In one embodiment the system comprises a personal computer having a commercially available telephony card and a cellular telephone carried by the user. The system calls the user after each scheduled workout and prompts the user to input whether they completed the workout. The system accepts and stores the input, calculates whether the user is achieving their workout goal, and gives the user positive or negative audio feedback based on whether the user is meeting their workout adherence target.

19 Claims, 10 Drawing Sheets

FIG. 4

| User : Table | | | | | | |
|---|---|---|---|---|---|---|
| UserPK | UserPhone | UserTarget | UserActual | UserFirstName | UserLastName |
| 1 | 2340696 | 80 | 67 | Jesse | Hercules |
| 3 | 2340875 | 1 | 1 | Dick | Hercules |
| 5 | 2340875 | 90 | 100 | Gail | Hercules |
| (AutoNumber) | 0 | 0 | 0 | | |

FIG. 5

| SchedulePK | UserFK | WorkoutDay | WorkoutHour | WorkoutMinute | WorkoutAMPM | Prognition | PromptMinute | PromptAMPM |
|---|---|---|---|---|---|---|---|---|
| 17 | 2 | Tuesday | 8 | 30 | AM | 9 | 15 | PM |
| 18 | 2 | Wednesday | 9 | 0 | PM | 10 | 0 | PM |
| 19 | 2 | Thursday | 11 | 15 | AM | 11 | 30 | AM |
| 20 | 2 | Friday | 11 | 15 | AM | 11 | 15 | AM |
| 21 | 2 | Saturday | 3 | 30 | PM | 3 | 45 | PM |
| 22 | 2 | Sunday | 4 | 45 | PM | 4 | 45 | PM |
| 23 | 3 | Monday | 9 | 30 | AM | 10 | 45 | AM |
| 24 | 3 | Saturday | 3 | 0 | PM | 3 | 30 | PM |
| 25 | 5 | Wednesday | 11 | 15 | AM | 12 | 0 | PM |
| 26 | 5 | Thursday | 12 | 15 | PM | 1 | 15 | PM |
| 27 | 2 | Monday | 8 | 15 | PM | 9 | 15 | PM |
| (AutoNumber) | 0 | | 0 | 0 | | 0 | 0 | |

FIG 6

| PerformancePK | ScheduleFK | WorkoutDate | WorkoutCompleted | PromptDate | PromptTime | WorkoutTime | WorkoutEndTime | UserFK | WorkoutDay |
|---|---|---|---|---|---|---|---|---|---|
| 4558 | 16 | 20040816 | 1 | 2 | | 125900 | 900 | 21 | |
| 4559 | 16 | 20040823 | 0 | 20040823 | 125900 | 125900 | 900 | 21 | |
| 4560 | 16 | 20040830 | 0 | 20040830 | 125900 | 125900 | 900 | 21 | |
| 4561 | 16 | 20040906 | 0 | 20040906 | 125900 | 125900 | 900 | 21 | |
| 4562 | 16 | 20040913 | 1 | 20040913 | 125900 | 125900 | 900 | 21 | |
| 4563 | 16 | 20040920 | 1 | 20040920 | 125900 | 125900 | 900 | 21 | |
| 4564 | 16 | 20040927 | | 20040927 | 125900 | 125900 | 900 | 21 | |
| 4565 | 16 | 20041004 | | 20041004 | 125900 | 125900 | 900 | 21 | |
| 4566 | 16 | 20041011 | | 20041011 | 125900 | 125900 | 900 | 21 | |
| 4567 | 16 | 20041018 | | 20041018 | 125900 | 125900 | 900 | 21 | |
| 4568 | 16 | 20041025 | | 20041025 | 125900 | 125900 | 900 | 21 | |
| 4569 | 16 | 20041101 | | 20041101 | 125900 | 125900 | 900 | 21 | |
| 4882 | 17 | 20040824 | | 20040824 | 211500 | 211500 | 83000 | 22 | |
| 4883 | 17 | 20040831 | | 20040831 | 211500 | 211500 | 83000 | 22 | |

| WorkoutDay | WorkoutHour | WorkoutMinute | WorkoutAM/PM | PromptHour | PromptMinute | PromptAM/PM |
|---|---|---|---|---|---|---|
| Tuesday | 8 | 30 | AM | 9 | 15 | PM |
| Wednesday | 9 | 0 | PM | 10 | 0 | PM |
| Thursday | 11 | 15 | AM | 11 | 30 | AM |
| Friday | 11 | 15 | AM | 11 | 15 | AM |
| Saturday | 3 | 30 | PM | 3 | 45 | PM |
| Sunday | 4 | 45 | PM | 4 | 45 | PM |
| Monday | 8 | 15 | PM | 9 | 15 | PM |
| * | 0 | 0 | | 0 | 0 | |

UserFirstName: Jesse
UserLastName: Hercules
UserPhone: 2340596

UserTarget: 80
UserActual: 67
UserPK: 2

Save Schedule

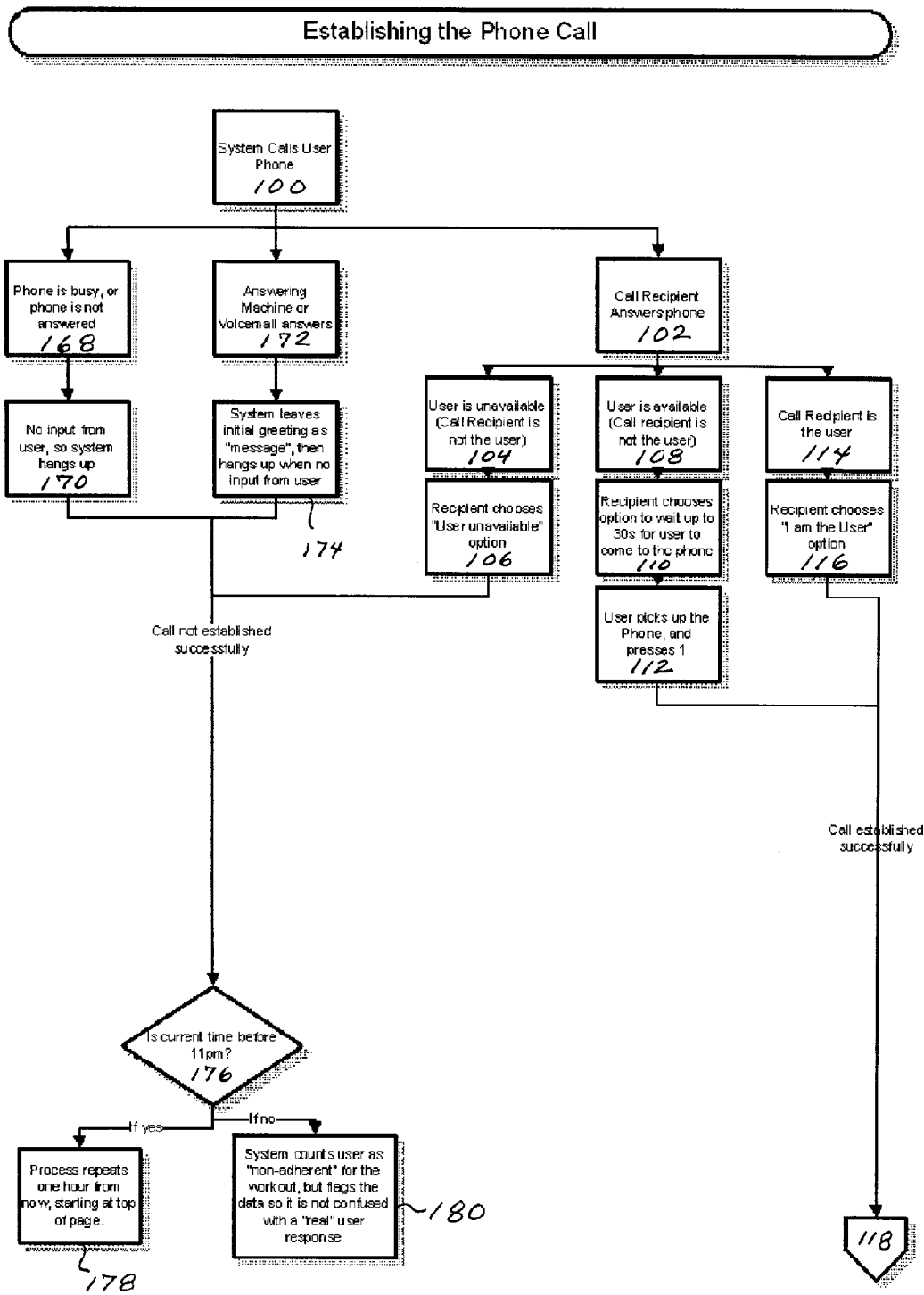

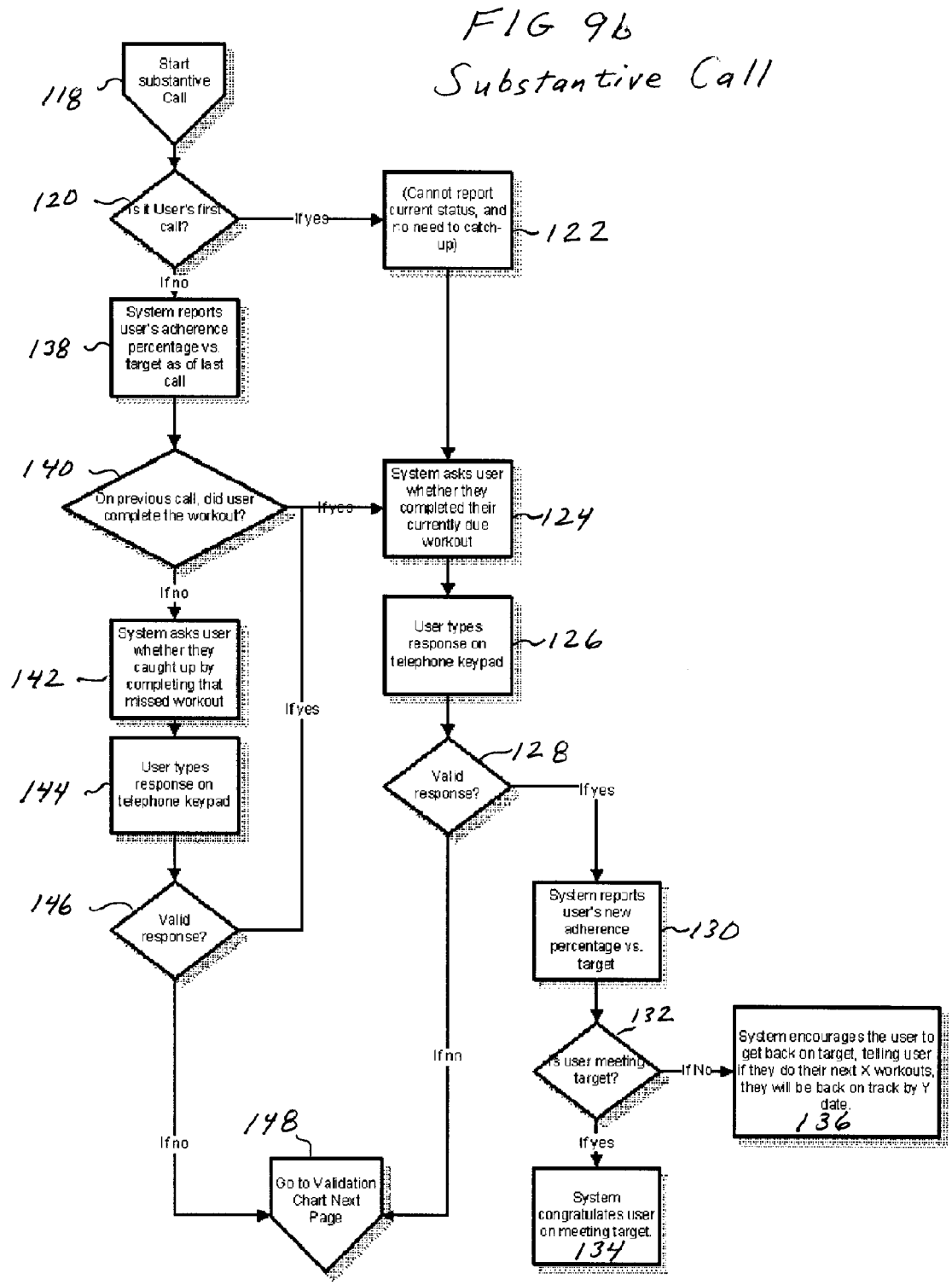

Validation

METHOD AND APPARATUS FOR MONITORING AND IMPROVING EXERCISE SCHEDULE COMPLIANCE

FIELD OF THE INVENTION

This patent relates to the field of exercise monitoring devices. More particularly, this patent relates to a system and apparatus for monitoring and improving a user's exercise compliance by providing the user with multiple forms of feedback designed to encourage adherence to an exercise schedule.

DESCRIPTION OF THE RELATED ART

Long-term consistent adherence to an exercise schedule is difficult for persons to achieve. This is true even when persons recognize and desire the health benefits that come from regular exercise. There are a number of reasons why people find consistent adherence difficult.

First, the feedback loop between exercise adherence to noticeable results (physiological changes such as less body fat or more muscle) is too slow to be behaviorally effective as reinforcement. Additional, faster reinforcement is needed.

Second, people find it difficult to hold themselves accountable to themselves. Someone, or something, must actively prompt the user, ask if the user did their scheduled workout, and keep track of their adherence statistics for them.

Third, people tend to see adherence as an all-or-nothing proposition. However, eighty or ninety percent adherence is a realistic goal, and far better than zero percent. Unfortunately people tend to give up on their entire program after external pressures cause them to miss a few workouts. At that point, users would benefit from an intervention that gives them a plan to get back to a realistic target adherence.

Thus it is an object of the present invention to remedy these three problems.

Another object of the present invention is to provide a system and apparatus for actively calling a user on the telephone after each scheduled exercise time, ask whether he did his workout, give immediate behavioral feedback, and inform him how his adherence compares with his target adherence. If he is below target, the system performs an intervention by telling him that if he completes a next given number of workouts he will be back on target by a given date.

Further and additional objects will appear from the description, accompanying drawings, and appended claims.

Various systems that monitor a user's dietary intake, caloric expenditure and/or exercise level and provide feedback regarding the user's progress toward a goal are known in the art. Some of them are described below.

Abrams et al. U.S. Pat. No. 5,673,691 discloses a hand held device that helps a user meet his or her exercise and/or dietary goals by applying behavior modification techniques. The device tracks the user's exercise and eating, determines the user's average daily caloric intake and expenditure, and tracks the user's weight to determine weekly weight loss. The device determines how the user is doing compared to his own dietary goals and provides positive feedback in the form of a message or a weight loss graph. Unlike the present invention, the device does not prompt the user to enter compliance data after each scheduled workout, but the system does prompt the user to exercise before each scheduled workout.

Douglas et al. U.S. Pat. No. 6,039,688 teaches a system for monitoring a patient's compliance with a doctor prescribed physical fitness program. Like the present invention, a user (typically the doctor) inputs an exercise schedule and the patient's goals. The system prompts the patient to input data relating to their adherence to the exercise program. The patient can input information into the system and the system can correlate the patient's progress toward their goal and provide ongoing multimedia feedback. Unlike the present invention, the device uses fixed time periods and milestones to measure user compliance and progress.

Buhler et al. U.S. Pat. No. 6,077,193 discloses a system that enables a user to create an exercise program with exercise goals and creates incentives to cause the user to stay with the exercise program. The system includes a "key" on which is stored the user's exercise program and progress in maintaining a fitness goal. The key can be inserted into a box installed on an exercise machine (such as a treadmill) to monitor the exercise performed. The user is awarded points for exercises performed as an incentive to comply with an exercise program.

Holland U.S. Pat. No. 6,607,483 discloses a hand held fitness monitoring system that can keep track of the physiological data, workout data and dietary data for a group of "members" participating in a fitness program. The system provides positive feedback by enabling a trainer to monitor changes in a member's physiological data so that the member can be informed of any progress.

Spyker U.S. Patent Document No. 2002/0107704A1 discloses a system for monitoring a user's exercise regimen. The user inputs his workout goals into the system, such as his desired weight or "physique level." After each workout the user inputs into the system his workout data, and the system logs the user's adherence level. The system can provide positive feedback in the form of an email. The system does not require the user to input a workout schedule as in the present invention, and does not automatically query the user after each scheduled workout time.

SUMMARY OF THE INVENTION

The present invention is a computer-based system for monitoring and improving a user's exercise schedule compliance by providing the user with multiple forms of feedback designed to encourage adherence to the exercise schedule. The system "calls" the user after each scheduled workout and prompts the user to input whether they completed the workout. The system accepts and stores the input, calculates whether the user is achieving their workout goal, and gives the user positive or negative feedback based on whether the user is meeting their workout adherence target.

The system hardware requirements include a data processing device such as a personal computer, a video display monitor, and means for inputting data (such as a keyboard). The computer should have an internal telephony card for two-way remote communication, and the user should be equipped with a telephone communication device such as a cell phone for receiving messages from the system and for inputting data (such as workout compliance) into the data processing device. Software requirements include a database management program (such as Microsoft Access), and computer telephony application software.

The system works in the following manner. First, the user inputs into the computer his or her identification, workout goal (percentage of scheduled workouts the user hopes to complete), workout schedule (days and times), and a workout prompt time.

At a specified time after each scheduled workout time the system queries the user whether he or she completed the scheduled workout. The user inputs compliance information (typically a yes or no response) into the system using a telephone. The system calculates the user's current percent compliance and notifies the user, providing positive reinforcement (if the user is meeting or exceeding their target goal) or negative reinforcement (if not).

THE DRAWINGS

FIG. 4 is a sample screen view of a User Table used in the exercise monitoring system of FIG. 1.

FIG. 5 is a sample screen view of a Schedule Table used in the exercise monitoring system of FIG. 1.

FIG. 6 is a sample screen view of a calendar table used in the exercise monitoring system of FIG. 1.

FIG. 7 is a sample screen view of a Performance table used in the exercise monitoring system of FIG. 1.

FIG. 8 is a sample user interface screen used in the exercise monitoring system of FIG. 1.

FIG. 9a is a flowchart for the establishing the phone call routine.

FIG. 9b is a flowchart for the substantive call routine.

DETAILED DESCRIPTION OF THE INVENTION

The present invention is a computer-based system for monitoring and improving a user's exercise compliance by providing the user with multiple forms of feedback designed to encourage adherence to an exercise schedule. The system "calls" the user after each scheduled workout and prompts the user to input whether they completed the workout. The system accepts and stores the input, calculates whether the user is achieving their workout goal, and gives the user positive or negative feedback based on whether the user is meeting their workout adherence target.

Hardware Requirements

Figure 1:
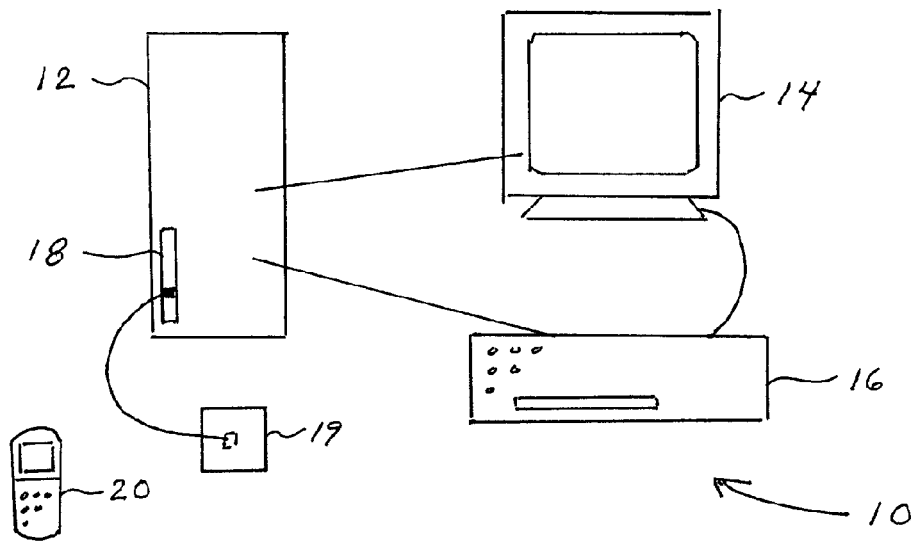
FIG. 1 is a schematic diagram of an exercise monitoring system according to the present invention.

One embodiment of the present invention is shown schematically in FIG. 1. The system 10 hardware requirements include a data processing device 12 such as a personal computer having means for receiving and storing personal information and exercise compliance information about a user, including a user's exercise schedule and compliance goal, a video display monitor 14 and means for inputting data 16 (such as a keyboard). The computer 12 should have means for remotely contacting the user after a scheduled exercise session, such as an internal telephony card 18 wired to an analog phone port 19 for two-way remote communication, and processing means for calculating the user's new rate of compliance to the exercise schedule based on the compliance information inputted by the user, comparing that new rate of compliance to the user's compliance goal, and means for generating an appropriate feedback message and transmitting that message to the user.

In one embodiment, the computer 12 is a commercially available Hewlett-Packard Pavilion a630n desktop PC running the Windows XP operating system with an Intel Runtime License serial port plug. The computer 12 must include means for remote communication with the user, such as a telephony card (such as Intel's D41-JCTLS 4-port telephony card) if the means of communication is by telephone or two-way paging, or a standard ethernet card if the means of communication is internet text messaging. If a telephony card is used, multiple phone lines per card and multiple cards per computer are possible.

The user should be equipped with a remote communication device 20 such as a cell phone for receiving messages from the computer 12 and for inputting data (such as exercise workout compliance) into the data processing device 12. Alternatively, the remote communication device can be a land line telephone, two-way pager, computer equipped with two-way internet text messaging capability, or any other suitable remote communication device.

The computer 12 may be any suitable data processing device, such as a commercially available Hewlett-Packard Pavilion a630n desktop PC running the Windows XP operating system with an Intel Runtime License serial port plug and an Intel D41-JCTLS 4-port telephony card installed. Multiple phone lines per card and multiple cards per computer are possible. Alternatively, and for illustration purposes only, the computer 12 can be equipped with Voice Over Internet Protocol or two-way internet text messaging.

Software Requirements

Figure 2:
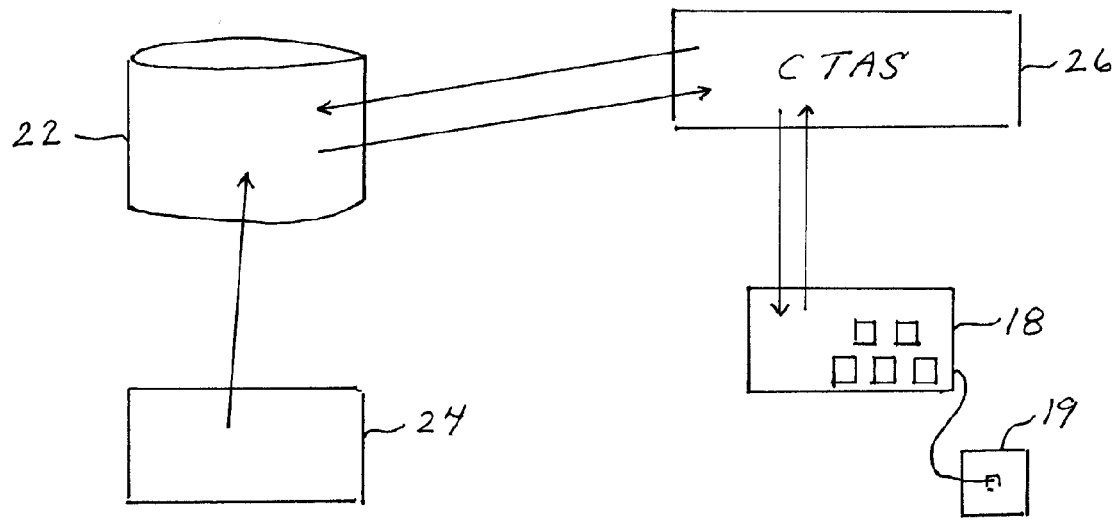
FIG. 2 is a schematic representation of the software requirements of the exercise monitoring system of FIG. 1.

As shown in FIG. 2, software requirements include, for example, a database management program 22 (such as Microsoft Access 2003), forms software 24 such as Microsoft Access forms 2003 with VBA macros, and executable computer telephony application software (CTAS) 26. The application software 26 controls the telephony card 18, makes calls to the user, and takes the user's telephone input.

Alternatively, the software can include means to communicate with the user via internet text messaging rather than telephony.

The application software was written in the Intel Computer Telephony Application Development Environment (CTADE) using Intel's proprietary programming language and flowcharting tools. The CTADE includes a compiler which was used to compile the application and make it executable on a PC.

Figure 3:
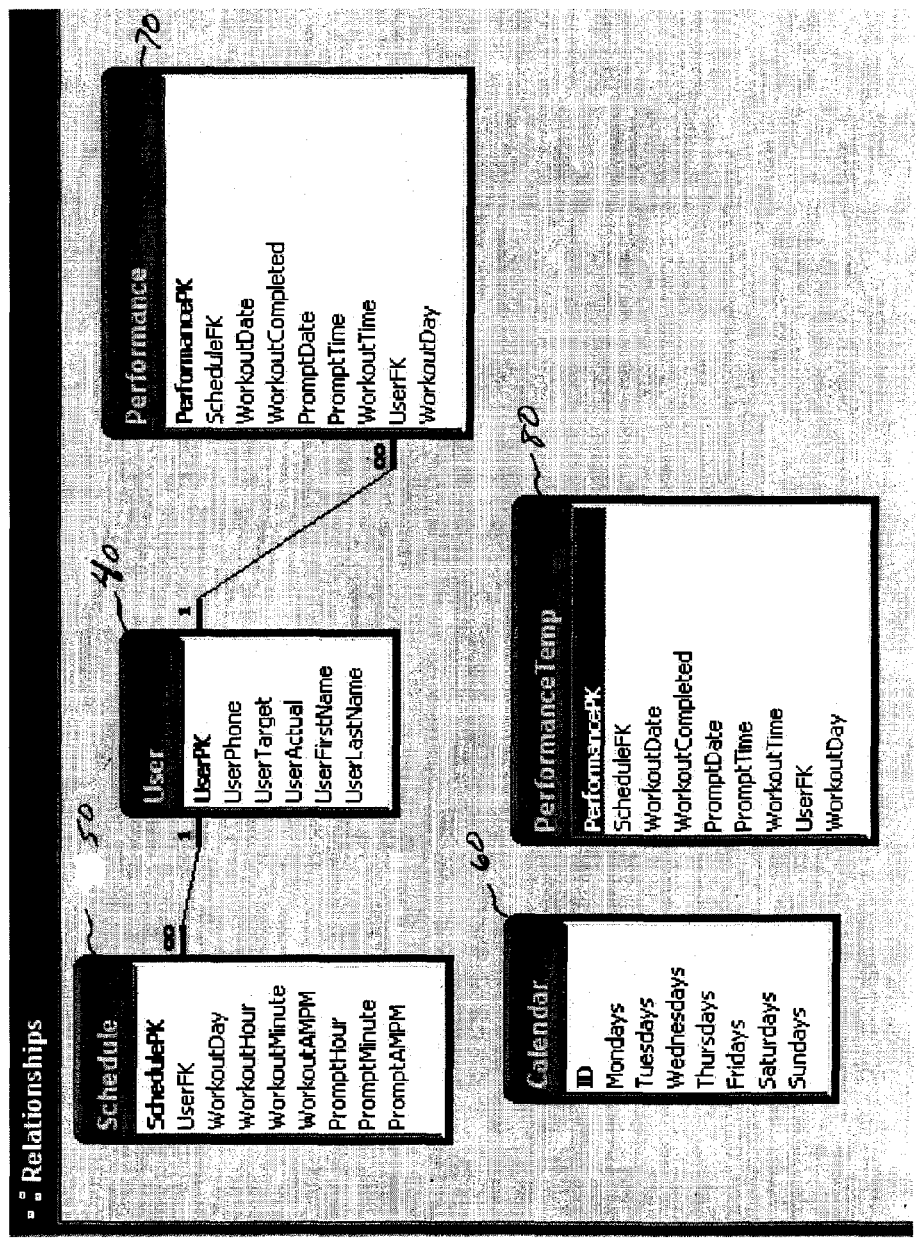
FIG. 3 is block diagram of the database structure of the exercise monitoring system of FIG. 1.

The database structure is depicted graphically in FIG. 3. The database comprises five tables: User Table 40, Schedule Table 50, Calendar Table 60, Performance Table 70 and PerformanceTemp Table 80. The purpose of each table will now be described:

The User Table (FIG. 4) holds each user's contact information, their target adherence percentage and their actual adherence percentage. Actual adherence percentage is updated by the CTAS program during every call to a user.

The Schedule Table (FIG. 5) holds the schedule input the user entered on the user interface form.

Figure 6:
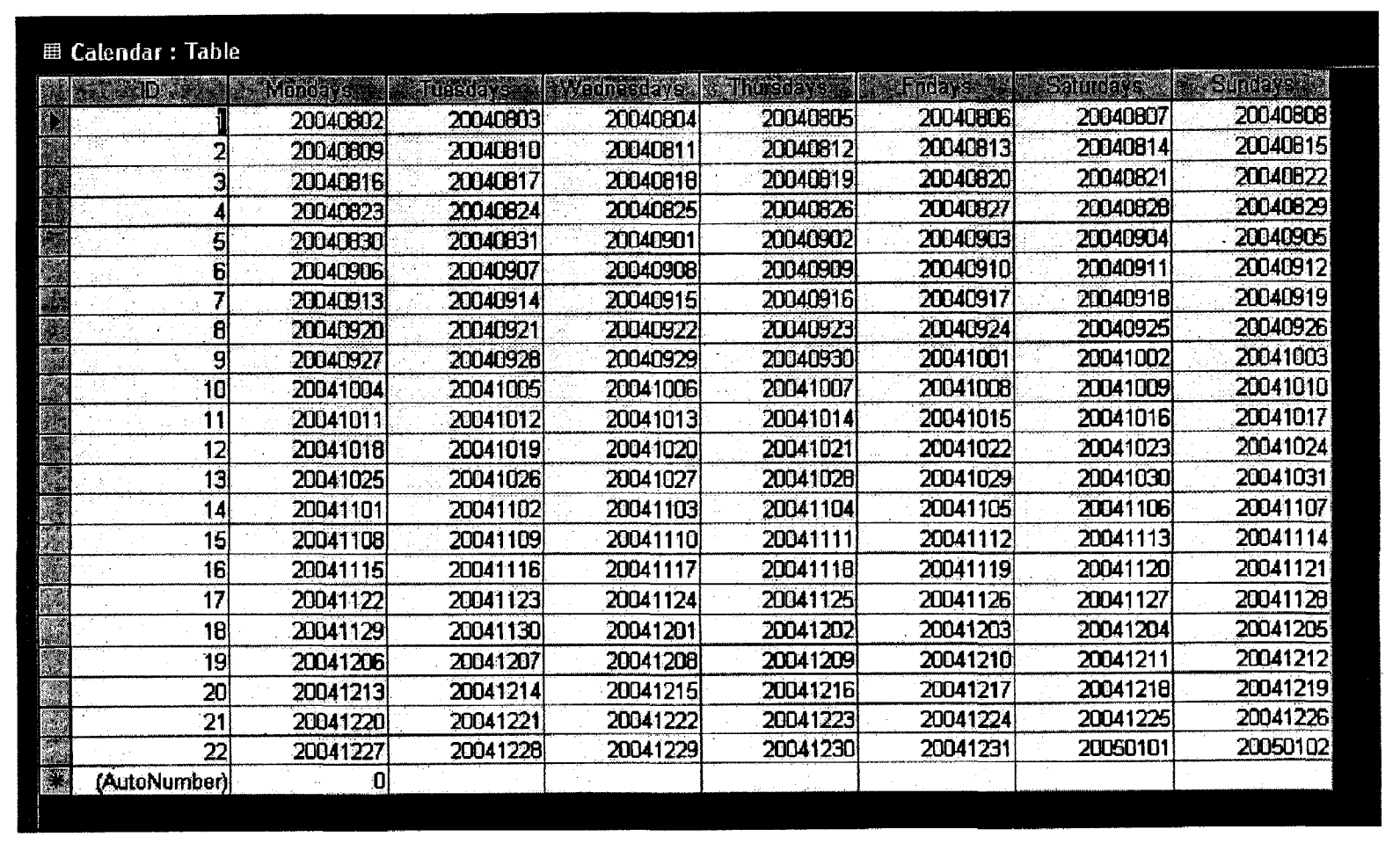

The Performance Table (FIG. 7) contains one row for each workout event the users have scheduled. This table is the result of transforming the Schedule Table (FIG. 5) into actual dates as shown in the Calendar Table (FIG. 6). Referring to the "Workout Completed" column, a "1" appears if the user completed a particular workout, a "0" if the user did not complete the workout and "NULL" if the user has yet to enter the information.

The PerformanceTemp Table (FIG. 3) is a table the CTAS program uses to calculate how many more workouts are needed to get the user back on his target percentage exercise goal. The program takes the user's last and next thirty days of workouts from the Performance Table and copies the data into the PerformanceTemp Table. Then within the PerformanceTemp table the program experimentally adds 1's to the WorkoutCompleted fields until the target percentage is reached. The program can then initiate an intervention subprogram (see Intervention Feature below) which notifies the user of both the date and the number of completed workouts needed to get back on target.

Manner of Operation

User Information Input

The system 10 works in the following manner. First, each user inputs into the computer 12 his or her identification data (e.g. name), workout goal (percentage of scheduled workouts the user hopes to complete), workout schedule (days and times), and workout prompt times.

A sample user interface screen is shown in FIG. 8. Referring to the sample user interface, the user adds one row of data for each scheduled workout. In that row, he fills in the day of the week, workout time, and a time he wishes to be called by the computer in regard to that workout. When done completing this form the user clicks "Save Schedule." The user is not required to fill in the "UserActual" or "UserPK" fields; these fields are there for software support reasons only.

When the user clicks "Save Schedule", the software adds rows to the Performance table (FIG. 7) which has one row for each workout event. The program can generate hundreds of workout events per year in the Performance table. Data on workout adherence is stored in the Performance table for each event.

Workout Inquiry and User Response

The system 10 can be used by multiple users at the same time. To accommodate multiple users, the database management program 22 runs in a continuous loop. At the beginning of the loop, the program 22 determines what call to make next. First, the program 22 looks in the database and finds the set of all calls it is to make. Then it picks the call with the earliest due date (basically, a first in, first out process). The computer stores the ID of the user who should be called about that workout, then dials the user.

At the time after each scheduled workout specified by the user, the computer 12 queries the user (typically via telephonic communication) whether he or she completed the scheduled workout. The user then inputs his or her compliance information (typically a yes or no response in the form of a 1 or 2 on the telephone dial) into the computer 12 using a telephone or other telecommunication device 20.

If at any time when the user is prompted for input the user presses a key other than 1 or 2, the program can play a message that explains that only 1 or 2 is an appropriate response. The computer can then repeat the workout inquiry.

If at any time when the user is being prompted for input the system does not "hear" the user input (caused, for example, by a bad telephone connection), the system gives the user three tries and then can move the prompt (inquiry) time one hour ahead of the current time and call back at that time.

If the user does not answer the telephone, the system can move the prompt time one hour ahead of the current time and call back at that time.

Calculation and Feedback

The computer 12 calculates the user's current percent compliance, typically for the last thirty days, and compares that percent to the user's target goal, and provides the user with feedback. The feedback may be positive reinforcement (if the user is meeting or exceeding their target goal) or negative reinforcement (if not). For example, if the user's actual exercise adherence percentage is below target, the program can determine how many workouts in a row the user will need to complete to get back on target. (See Intervention Feature below). If the user is at or above the target percentage, the computer can play a positive verbal or musical message praising the user for being on track.

After going through this inquiry, calculation and feedback routine the computer program then starts its loop from the beginning.

In addition to the basic features described above, the system 10 can also have the following optional features:

Rolling Basis Feature

Unlike some previous compliance systems which can only handle a fixed start date, the present system 10 has the capability of handling a movable start date. With the "rolling basis" feature, the system software has the capability of calculating a new rate of compliance to an exercise schedule based on a percentage of times the user has completed scheduled exercise sessions during a previous predetermined number of days, rather than from a set start date. This feature keeps the focus on recent performance because old performances—good and bad—drop out of the calculation as new ones are added.

Standing Start With Rolling Basis Feature

The computer software also has the capability of calculating a rate of compliance based on the percentage number of times a user has completed a scheduled exercise session during the lesser of either a previous predetermined number of days or the number of days the user has used the system. This makes the compliance rate very sensitive to each episode of compliance at first, automatically transitioning to normal sensitivity as use continues. For example, if after the first two scheduled two exercise sessions the user has completed only one of two workouts, the user's compliance rate will be 50 percent. Completing the third scheduled exercise session (and responding positively to the system's inquiry) will increase the compliance rate to 66 percent, a significant increase. However, as time goes on the compliance rate will be much less sensitive to the latest positive—or negative—result.

Intervention Feature

It can be useful psychologically for a user to know how quickly she can "get back on target", or increase her compliance to her set goal. To that end, the computer 12 may include means for calculating a number of workouts after which the user will be next in compliance if the user responds positively to each future computer inquiry through the number of workouts. The computer can provide both the date and the number of completed workouts needed to get back on target.

Catch Up Feature

The computer can be programmed to give the user a chance to catch up if she misses a workout, but the catch up period is limited to the time between the missed workout and the next workout.

Before dialing up a user after a workout, the computer looks to see whether the user completed the penultimate (next to last) workout. If the penultimate workout has not been completed (that is to say, the user did not respond positively when queried about the workout), the program goes through a "catch up" routine. As part of the catch-up routine the computer queries the user whether he completed an exercise session in the time between the penultimate scheduled exercise session and the most recent scheduled exercise session. The data from this inquiry is included in the user's compliance data and used for compliance calculations.

Non-optimized Target Feature

The program allows a user to set any exercise compliance goal, from 100% (optimized target) to anything less than 100% (non-optimized target). Thus a user can set a goal that is realistic and will provide real physiological benefits.

EXAMPLES

In the example computer/user audio exchanges that follow, the system 10 uses a combination of prerecorded audio files (regular text below), numbers read from the user's database (bold text below), and pre-recorded audio files that are selected based on values in the user's database (italicized text below). For example, the system 10 chooses one of seven pre-recorded audio files (Monday, Tuesday, etc.) based on the workout's appropriate day of the week.

Example 1

Initial Greeting Audio, User Makes Workout, User Exceeding Target (Establishing the phone call routine (FIG. 9*a*): The system calls the user (Step 100). The user's phone rings and the user answers the phone (Step 102). After establishing that the call recipient is the user (Steps 104–116, the system initiates a substantive calling routine 118 (FIG. 9*b*).

After determining that the call is the user's first call from the system (Step 120), the system skips the reporting routine 122 and proceeds with the inquiry step 124 as follows.)

System: Hello, this is your health club calling. Welcome to the BE FIT system. We think that using this system will help you stay on your fitness plan, so that you can achieve your fitness goals. (pause) Did you complete your Monday 8 o'clock AM workout?

User: (The user indicates yes by pressing one (Step 126).)

System: (The system recognizes the valid response, step 128, and proceeds with the reporting and positive feedback subroutine steps 130–134.) Thank you. You have now completed 100 percent of your scheduled workouts for the last 30 days, and you are meeting your target of 60 percent. Good job! Take a second to enjoy the feeling of being on track to achieve your goals.

Example 2

User Misses a Workout, User Below Target (System calls the user (Step 100). User's phone rings and the user answers the phone (Step 116). After determining that this is not the user's first call (Step 120), the system initiates reporting subroutine 138. After determining that the user completed his workout on the previous call (Step 140), the system initiates inquiry step 124.

System: Hello, this is your health club calling. Last time we talked, you had completed 100 percent of your scheduled workouts, and you were meeting your target of 60 percent. (pause) Did you complete your Tuesday, 8 o'clock AM workout? Press one if you did, press two if you did not.

User: (The user indicates no by pressing two.)

System (Initiating Steps 130, 132, and the Intervention Step 136. The system is using an optional form of Step 130 to remind the user that Catch-Up Steps 140–146 will be available on the next call.): Thank you. Remember that you can still catch up. When I call you about your next scheduled workout, I will ask you whether you were able to catch up by completing this workout. You have now completed 50 percent of your scheduled workouts for the last 30 days, but you are not meeting your target of 60 percent. But don't give up. If you complete your next 1 workouts, you will be back on target by Aug. 18th, 2004.

Example 3

Catch Up Feature (System calls the user (Step 100). User's phone rings and the user answers the phone (Steps 102, 114, 116). After determining that this is not the user's first call (Step 120), the system initiates reporting subroutine 138. After determining that the user did not completed his workout on the previous call (Step 140), the system initiates catch up subroutine 142–146))

System: Hello, this is your health club calling. Last time we talked, you had completed 50 percent of your scheduled workouts, but you were not meeting your target of 60 percent. (pause) Did you catch up by completing your Tuesday, 8 o'clock AM workout? Press one if you did, press two if you did not.

User: (The user indicates yes by pressing one. (Step 144)) (After obtaining the user's response to the catch-up inquiry, the computer proceeds with the normal Step 124 inquiry.)

System: Thank you. Did you complete your Wednesday, 8 o'clock AM workout? Press one if you did, press two if you did not.

User: (The user indicates yes by pressing one (Step 144).)

System: Thank you. You have now completed 100 percent of your scheduled workouts for the last 30 days, and you are not meeting your target of 60 percent. Good job! Take a second to enjoy the feeling of being on track to achieve your goals.

Figure 9C:
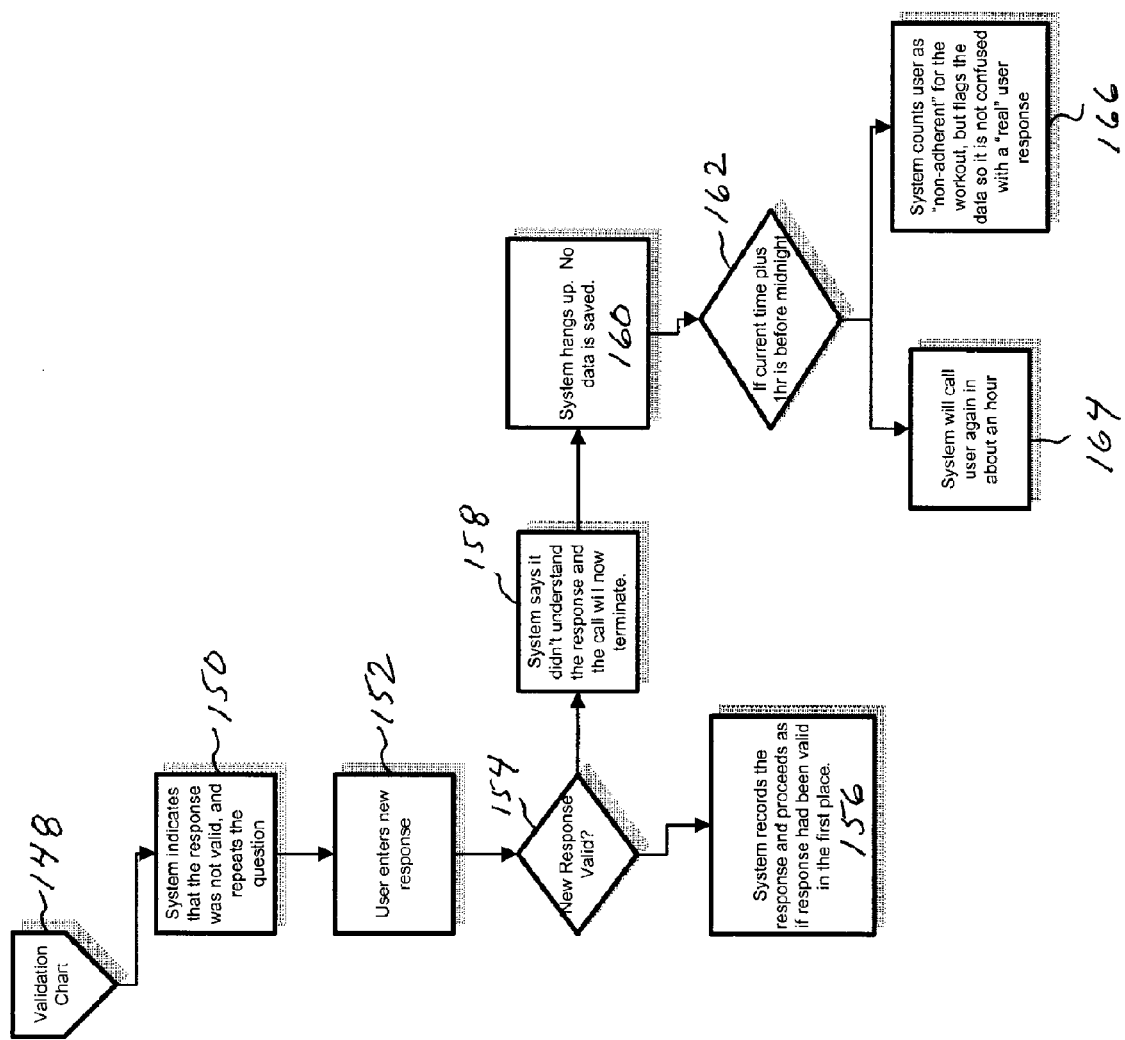
FIG. 9c is a flowchart for the validation routine.

The system software includes a validation routine that is initiated when the user does not give a valid response to an inquiry (FIG. 9*c*, steps 148–166). The system software also includes subroutines that are initiated when the user's phone is busy or an answering machine or voicemail answers (FIG. 9*a*, steps 168–180).

Other modifications and alternative embodiments of the invention are contemplated which do not depart from the scope of the invention as defined by the foregoing teachings and appended claims. It is intended that the claims cover all such modifications that fall within their scope.

What is claimed is:

1. A computer-based system for monitoring and increasing a user's exercise program compliance, the system comprising:
    a computer having means for receiving and storing personal information about the user, including the user's exercise schedule and compliance goal; means for remotely contacting the user after a scheduled exercise session and inquiring of a user's compliance during a last scheduled exercise session; means for receiving and storing a user's compliance information; processing means for calculating a user's new rate of compliance to the exercise program based on the compliance information received remotely from the user, comparing that new rate of compliance to the user's compliance goal and generating a feedback message; and means for transmitting that feedback message to the user; and
    remote means by which the user can receive from the computer a compliance inquiry, input to the computer the user's compliance information, and receive from the computer the feedback message.

2. The computer-based system of claim 1 wherein the remote means comprises a land telephone.

3. The computer-based system of claim 1 wherein the remote means comprise a cell phone.

4. The computer-based system of claim 1 wherein the remote means comprises a two-way pager.

5. The computer-based system of claim 1 wherein the remote means comprises a computer equipped with two-way internet text messaging capability.

6. The computer-based compliance system of claim 1 wherein the user's compliance goal is less than 100%.

7. The computer-based system of claim 1 wherein the new rate of compliance to the exercise program is calculated as the percentage of times the user has completed scheduled exercise sessions during the previous predetermined number of days.

8. The computer-based system of claim 1 wherein the new rate of compliance is calculated as the percentage of times the user has completed scheduled exercise sessions during the lesser of either the previous predetermined number of days or the number of days the user has used the computer-based system.

9. The computer-based system of claim 1 wherein the processing means includes means for calculating a date when the user will be next in compliance if the user completes each future scheduled exercise session through said date and wherein the feedback message includes said date.

10. The computer-based system of claim 1 wherein the processing means includes means for calculating a number of workouts after which the user will be next in compliance if the user completes each future scheduled exercise session through said number of workouts and wherein the feedback message includes said number of workouts.

11. The computer-based system of claim 1 wherein the processing means includes means for determining whether the user did not complete a penultimate scheduled exercise session and means for generating a catch up message for the user after a most recent scheduled exercise session inquiring whether the user completed an exercise session in a time between the penultimate scheduled exercise session and the most recent scheduled exercise session, and means for calculating user compliance including a user's response to the catch up message.

12. The computer-based system of claim 1 wherein the means for remotely contacting the user comprises a telephony card or an ethernet card.

13. A method of monitoring and increasing the compliance of a user following an exercise program, the method comprising the steps of:
the user inputting into a computer system a user's identification data, the user's exercise schedule and an exercise compliance goal;
after each scheduled exercise session the computer system requesting the user to input into the computer system whether the user did or did not exercise during a scheduled exercise session;
the user entering a yes or no response into the computer system via a remote device;
the computer system calculating the percentage of times the user has completed scheduled exercise sessions and comparing that percentage compliance to the user's exercise compliance goal; and
the computer system providing the user with remote feedback regarding whether the user is currently in compliance with the user's exercise compliance goal.

14. The method of claim 13 wherein during the calculating step the computer calculates a percentage of times the user has completed scheduled exercise sessions during a previous predetermined number of days.

15. The method of claim 13 wherein during the calculating step the computer calculates a percentage of times the user has completed scheduled exercise sessions during the lesser of either a previous predetermined number of days or a number of days the user has followed the exercise program.

16. The method of claims 14 or 15 wherein during the calculating step the computer calculates a date when the user will next be in compliance if the user completes each future scheduled exercise session after said scheduled exercise session and through said date and during the providing step the computer provides the user feedback identifying said date.

17. The method of claims 14 or 15 wherein during the calculating step the computer calculates a number of workouts after which the user will next be in compliance if the user completes each future scheduled exercise session through said number of workouts and during the providing step the computer provides the user feedback identifying said number of workouts.

18. The method of claim 13 wherein if the user did not complete a penultimate scheduled exercise session, the computer generates a catch up message inquiring whether the user completed an exercise session in a time between the penultimate scheduled exercise session and the most recent scheduled exercise session, and the computer calculates user compliance including the user's response to the catch up message.

19. The method of claim 13 wherein the exercise compliance goal is less than 100%.

* * * * *